United States Patent
Zhou

(10) Patent No.: US 10,201,370 B2
(45) Date of Patent: Feb. 12, 2019

(54) ANTI-REVERSE APPARATUS FOR TROCAR AND TROCAR

(71) Applicant: Guangzhou T.K Medical Instrument Co., Ltd., Guangzhou (CN)

(72) Inventor: Xing Zhou, Guangzhou (CN)

(*) Notice: Subject to any disclaimer, the term of this patent is extended or adjusted under 35 U.S.C. 154(b) by 0 days.

(21) Appl. No.: 15/600,230

(22) Filed: May 19, 2017

(65) Prior Publication Data

US 2017/0252061 A1     Sep. 7, 2017

Related U.S. Application Data

(63) Continuation of application No. PCT/CN2015/095029, filed on Nov. 19, 2015.

(30) Foreign Application Priority Data

Feb. 7, 2015 (CN) .......................... 2015 1 0067832

(51) Int. Cl.
*A61B 17/34* (2006.01)
*A61B 17/02* (2006.01)
(Continued)

(52) U.S. Cl.
CPC ...... *A61B 17/3417* (2013.01); *A61B 17/0218* (2013.01); *A61B 17/3423* (2013.01);
(Continued)

(58) Field of Classification Search
CPC ............ A61B 17/0218; A61B 17/3423; A61B 17/3462; A61B 17/3417; A61B 2017/3419; A61B 2017/00469; A61B 2017/00464

See application file for complete search history.

(56) References Cited

U.S. PATENT DOCUMENTS

| 6,569,119 B1* | 5/2003 | Haberland | A61B 17/3462 604/167.03 |
| 2005/0070851 A1* | 3/2005 | Thompson | A61B 17/3462 604/167.03 |

(Continued)

FOREIGN PATENT DOCUMENTS

| CN | 102429707 A | 5/2012 |
| CN | 104068921 A | 10/2014 |

(Continued)

OTHER PUBLICATIONS

Guangzhou, International Search Report and Written Opinion, PCT/CN2015/095029, dated Feb. 6, 2016, 13 pgs.

(Continued)

*Primary Examiner* — Theodore Stigell
(74) *Attorney, Agent, or Firm* — Morgan, Lewis & Bockius LLP

(57) ABSTRACT

An anti-reverse apparatus includes a latch capable of stopping an end sealing piece from moving reversely, and a loose switch capable of relieving a stop action by the latch on the reverse movement of the end sealing piece. Limitation of the latch on the reverse movement of the end sealing piece can be relieved by pressing the loose switch down. When the end sealing piece is detachably mounted at a near end of a sleeve in a rotating manner, the latch can stop reverse movement causing loosening of the end sealing piece and prevent air leakage or the end sealing piece from loosening from the near end of the sleeve. When the loose switch is pressed down, limitation of the latch on the reverse movement of the end sealing piece can be relieved, and the end sealing piece can be detached from the near end of the sleeve.

4 Claims, 6 Drawing Sheets

(51) Int. Cl.
*A61B 17/00* (2006.01)
*A61M 25/00* (2006.01)

(52) U.S. Cl.
CPC ...... *A61B 17/3462* (2013.01); *A61B 17/3474* (2013.01); *A61B 2017/0046* (2013.01); *A61B 2017/00464* (2013.01); *A61B 2017/00469* (2013.01); *A61B 2017/00477* (2013.01); *A61B 2017/3419* (2013.01); *A61M 25/0074* (2013.01)

(56) References Cited

U.S. PATENT DOCUMENTS

| | | | |
|---|---|---|---|
| 2006/0264992 A1 | 11/2006 | Franer et al. | |
| 2007/0088277 A1 | 4/2007 | McGinley et al. | |
| 2012/0010569 A1* | 1/2012 | Parihar | A61B 17/3421 604/167.01 |
| 2013/0237902 A1 | 9/2013 | McGinley et al. | |
| 2015/0031958 A1 | 1/2015 | Kleyman | |

FOREIGN PATENT DOCUMENTS

| | | |
|---|---|---|
| CN | 204500899 U | 7/2015 |
| JP | 2009-502211 A | 1/2009 |
| WO | WO2014/052532 | 4/2014 |

OTHER PUBLICATIONS

Guangzhou, International Preliminary Report on Patentability, PCT/CN2015/095029, dated Aug. 8, 2017, 5 pgs.

Guangzhou, Notice of Reasons for Rejection, JP2017-35762, dated May 9, 2018, 8 pgs.

Guangzhou, Notice of Reasons for Rejection, JP2017-35762, dated Oct. 15, 2018, 7 pgs.

* cited by examiner

ANTI-REVERSE APPARATUS FOR TROCAR AND TROCAR

PRIORITY CLAIM AND RELATED APPLICATIONS

This application is a continuation application of PCT Patent Application No. PCT/CN2015/095029 entitled "ANTI-REVERSING DEVICE OF TROCAR, AND TROCAR" filed on Nov. 19, 2015, which claims priority to Chinese Patent Application No. 201510067832.X, entitled "ANTI-REVERSE APPARATUS FOR TROCAR AND TROCAR" filed on Feb. 7, 2015, both of which are incorporated by reference in their entirety.

TECHNICAL FIELD

The disclosed implementations relate generally to a laparoscopic surgery instrument, and in particular, to an anti-reverse apparatus for a trocar used in a laparoscopic surgery and a trocar.

BACKGROUND

A laparoscopic surgery is applied more and more widely. In order to avoid iatrogenic infection, the consumption of a disposable trocar used in the laparoscopic surgery is increasingly greater. The trend of simplifying the structure, reducing the cost, improving the performance on the basis of ensuring using performance has already become an improvement direction of the trocar.

In the laparoscopic surgery, when passing through the disposable trocar, a surgical instrument carries out an entry-exit reciprocating motion as well as a rotating motion. When a surgical instrument having a large diameter, such as a 10 mm or 12 mm surgical instrument, passes through a surgical instrument through hole of a 4 mm end sealing ring, the end sealing ring will generate a large surrounding force on the surgical instrument. In this case, the rotating motion of the surgical instrument inserted into the trocar may cause co-rotation of an end sealing piece and the instrument, thus causing loose between the end sealing piece and a near end of a sleeve of the trocar due to reverse movement so as to result in air leakage, or separating or disengaging the end sealing piece from the near end of the sleeve of the trocar so as to affect use of the trocar. Therefore, an improvement is needed.

SUMMARY

An anti-reverse apparatus for a trocar is provided in the present application. A trocar 100 is composed of a trocar rod 101 and a sheath 102.

A. The sheath 102 of the trocar includes an end sealing piece 1, a sleeve 2 and an anti-reverse apparatus 3.

B. The end sealing piece 1 is detachably mounted at a near end of the sleeve 2.

C. The anti-reverse apparatus 3 includes a latch 31 capable of stopping the end sealing piece 1 from moving reversely, and a loose switch 32 capable of relieving a stopping action exerted by the latch 31 on the reverse movement of the end sealing piece 1. By pressing the loose switch 32 down, limitation of the latch 31 on the reverse movement of the end sealing piece 1 can be relieved.

The latch 31 is disposed on a side surface 21 of the near end of the sleeve 2, and the loose switch 32 is disposed on a side surface 11 of a housing of the end sealing piece 1, the loose switch 32 corresponding to the latch 31 in position.

The latch 31 and the loose switch 32 are disposed on the side surface 11 of the housing of the end sealing piece 1 separately, the latch 31 is inlaid in a positioning concave groove 21-1 of the side surface 21 of the near end of the sleeve 2 to form concave-convex engagement, and the latch 31 can be pulled out of the positioning concave groove 21-1 by pressing the loose switch 32 down.

The end sealing piece 1 is detachably mounted at the near end of the sleeve 2 by means of a rotary inlaid type concave-convex engagement structure.

The end sealing piece 1 is detachably mounted at the near end of the sleeve 2 by means of a threaded structure.

A trocar is provided. The trocar includes the anti-reverse apparatus according to claim 1.

The anti-reverse apparatus 3 of the present application includes a latch 31 capable of stopping an end sealing piece 1 from moving reversely, and a loose switch 32 capable of relieving a stopping action exerted by the latch 31 on the reverse movement of the end sealing piece 1. By pressing the loose switch 32 down, limitation of the latch 31 on the reverse movement of the end sealing piece 1 can be relieved. When the end sealing piece 1 is detachably mounted at the near end of the sleeve 2 in a rotating manner, the latch 31 of the anti-reverse apparatus 3 can stop reverse movement resulting in loosening of the end sealing piece 1 and prevent air leakage or prevent the end sealing piece 1 from loosening from the near end of the sleeve 2. When the loose switch 32 is pressed down, limitation of the latch 31 on the reverse movement of the end sealing piece 1 can be relieved, and the end sealing piece 1 is detached from the near end of the sleeve 2.

The trocar 100 of the present application includes the anti-reverse apparatus 3.

The end sealing piece 1 of the trocar 100 of the present application can be detachably mounted at the near end of the sleeve 2 in a rotating manner. For example, the end sealing piece is rotated clockwise, a connecting convex step 12 of the end sealing piece 1 slides into a connecting concave groove 22 at the near end of the sleeve 2, and the end sealing piece 1 and the sleeve 2 are connected together in a concave-convex engagement manner. The latch 31 of the anti-reverse apparatus 3 warps up, and engages with a positioning block 11-1 on the end sealing piece 1, such that the end sealing piece 1 cannot be rotated anticlockwise, thus stopping reverse movement capable of resulting in loosening of the end sealing piece 1, namely anticlockwise rotation of the end sealing piece 1.

When the end sealing piece 1 of the trocar 100 of the present application needs to be detached from the near end of the sleeve 2, the loose switch 32 is pressed down, the latch 31 of the anti-reverse apparatus 3 is pressed down, and cannot engage with the positioning block 11-1 on the end sealing piece 1, such that the end sealing piece 1 can be rotated anticlockwise, that is, the end sealing piece 1 is detached from the near end of the sleeve 2 by means of reverse movement.

The anti-reverse apparatus 3 can stop reverse movement resulting in loosening of the end sealing piece 1 and prevent air leakage or prevent the end sealing piece 1 from loosening from the near end of the sleeve 2. The defects of a conventional trocar are overcome, and the reliability of the trocar is improved.

BRIEF DESCRIPTION OF THE DRAWINGS

FIG. 1-1 is an A-A sectional view of FIG. 1.

FIG. 1-2 is a B enlarged view of FIG. 1-1.

FIG. 1-3 is a schematic structural diagram of an end sealing piece of a trocar of FIG. 1.

FIG. 1-4 is a C enlarged view of FIG. 1-3.

FIG. 1-5 is a schematic structural diagram of a sleeve of a trocar of FIG. 1.

FIG. 1-6 is a D enlarged view of FIG. 1-5.

FIG. 1-7 is an exploded view of FIG. 1.

FIG. 2 is a schematic structural diagram of an inlaid type anti-reverse apparatus and a trocar of the present application.

FIG. 2-1 is an E enlarged view of FIG. 2.

FIG. 2-2 is a schematic structural diagram of an end sealing piece of a trocar of FIG. 2.

FIG. 2-3 is an F enlarged view of FIG. 2-2.

FIG. 2-4 is a schematic structural diagram of a sleeve of a trocar of FIG. 2.

FIG. 2-5 is a G enlarged view of FIG. 2-4.

FIG. 2-6 is an exploded view of FIG. 2.

In the foregoing accompanying drawings:

100 is a trocar of the present application, 101 is a trocar rod of a trocar of the present application, and 102 is a sheath of a trocar of the present application.

1 is an end sealing piece, and 2 is a sleeve.

11 is a side surface of a housing of an end sealing piece, 11-1 is a positioning block on a side surface of a housing of an end sealing piece, and 12 is a connecting convex step of an end sealing piece.

21 is a side surface of a sleeve, 21-1 is a positioning concave groove on a side surface of a sleeve, and 22 is a connecting concave groove of a sleeve.

31 is a latch, 32 is a loose switch, 33 is a rotary shaft, and 34 is a shell.

DESCRIPTION OF EMBODIMENTS

Figure 1:
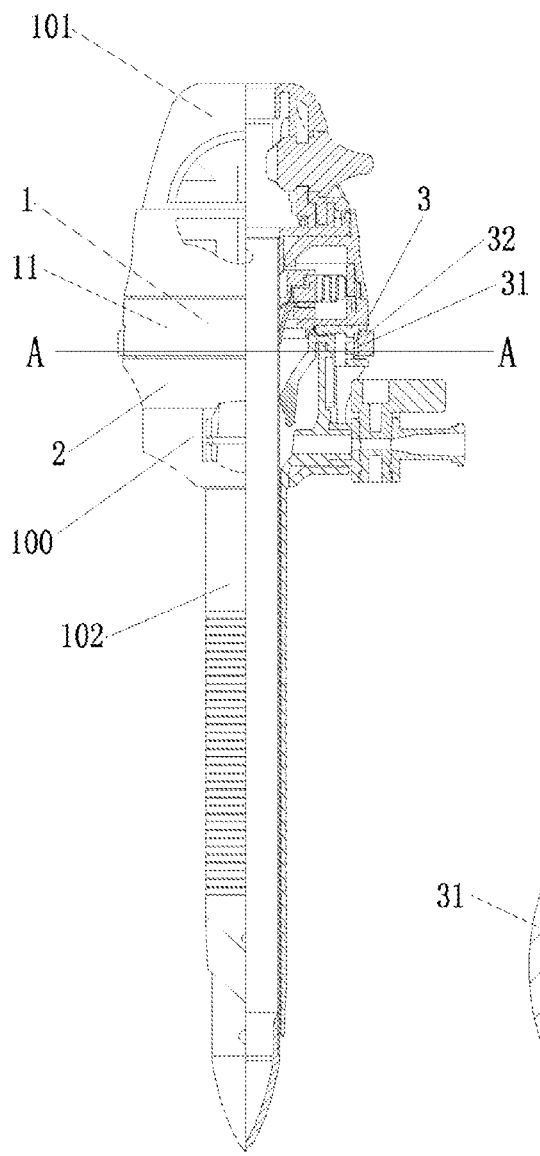
FIG. 1 is a schematic structural diagram of an engagement type anti-reverse apparatus and a trocar of the present application.
Figure 1:
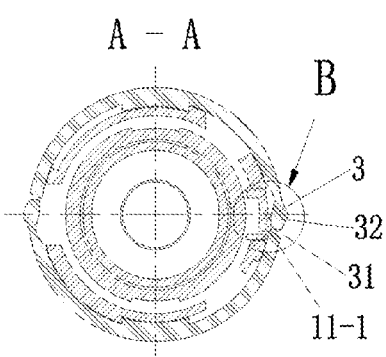
Figures 1, 2:
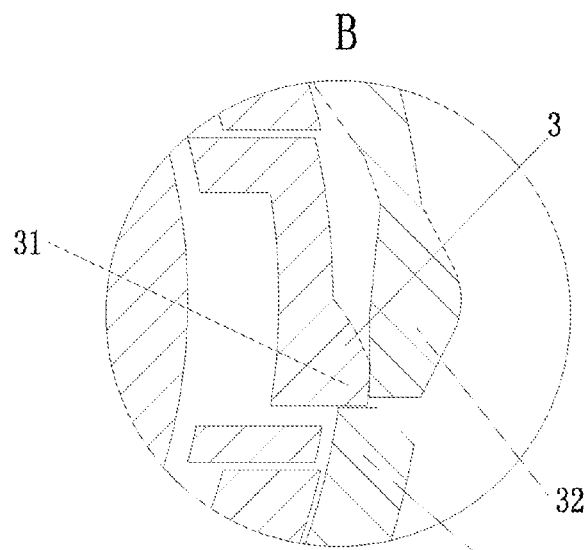
Figures 1, 2, 3:
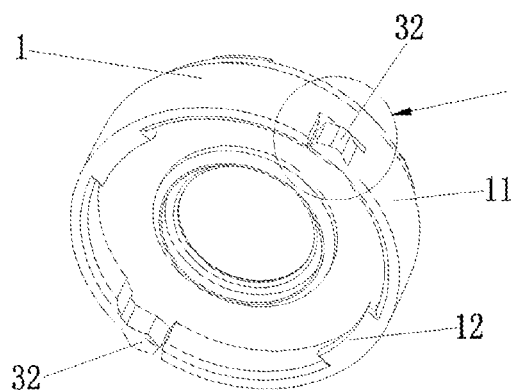
Figures 1, 2, 3, 4:
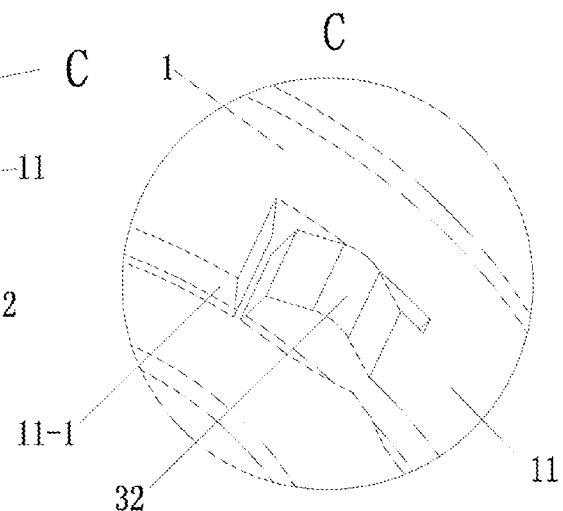
Figures 1, 2, 3, 4, 5:
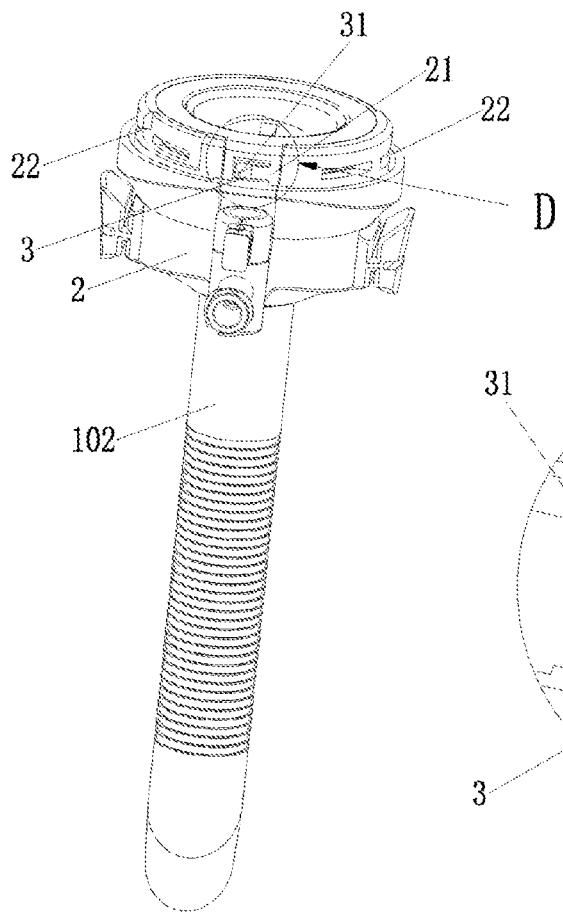
Figures 1, 2, 3, 4, 5, 6:
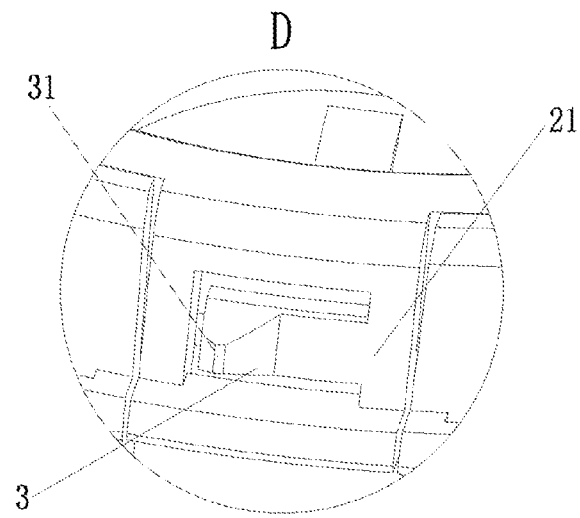
Figures 1, 2, 3, 4, 5, 6, 7:
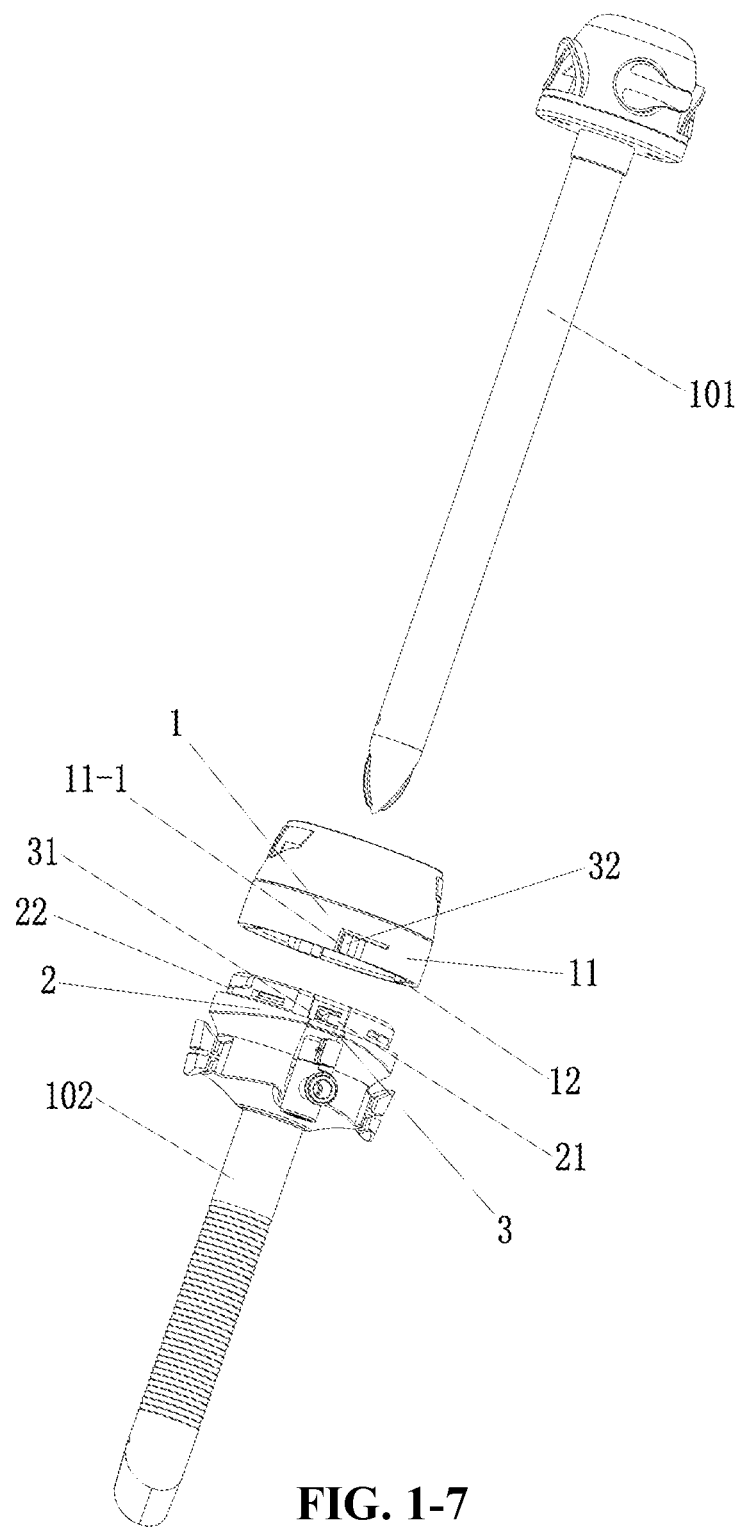
Figures 1, 2:
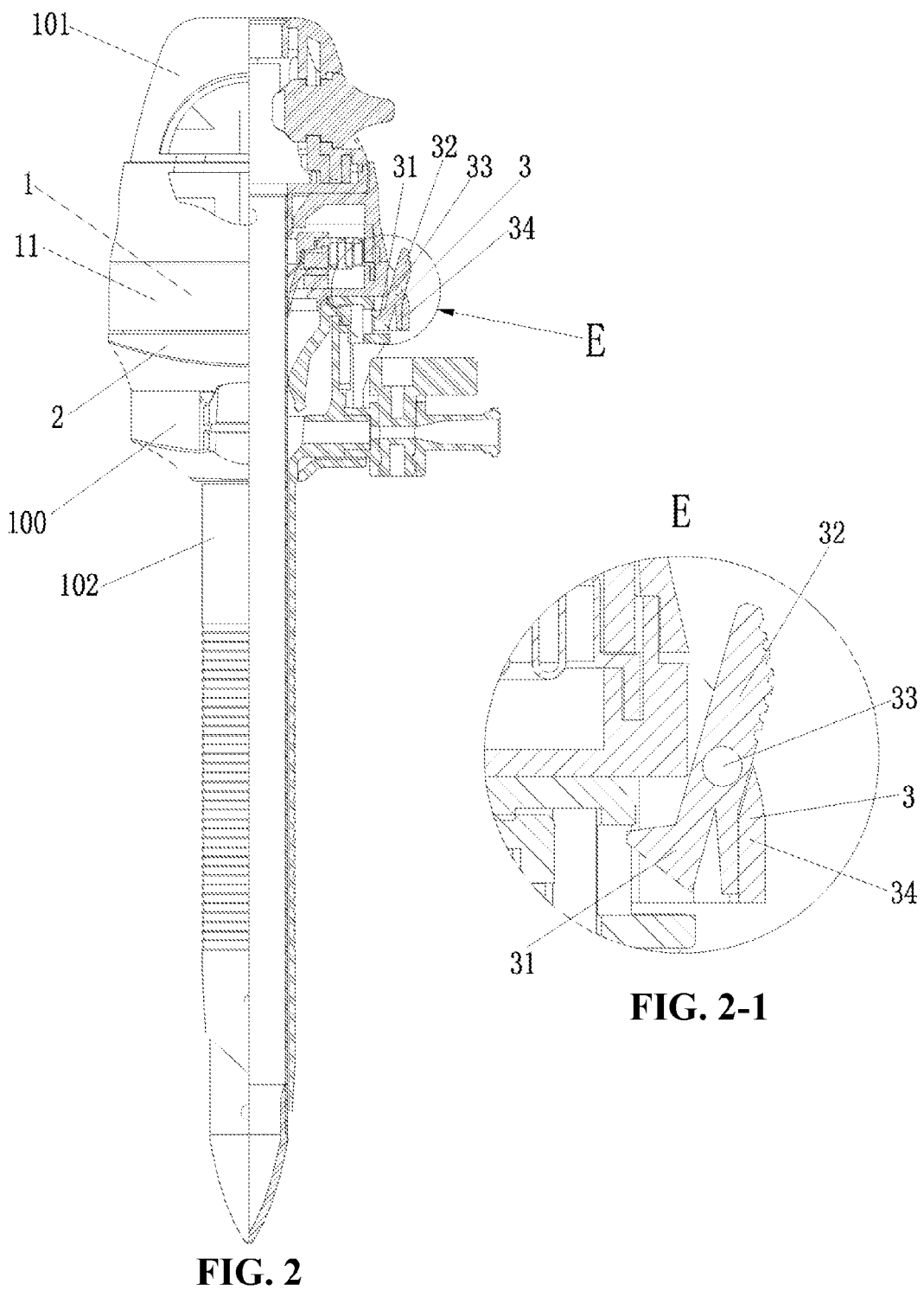
Figure 2:
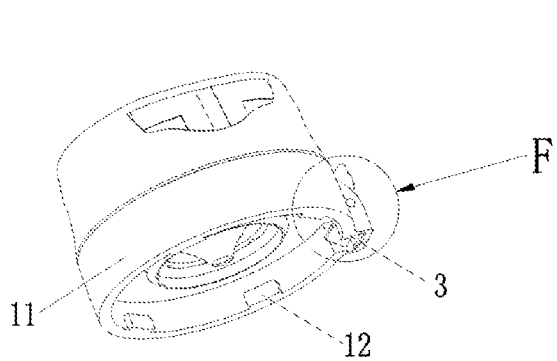
Figures 2, 3:
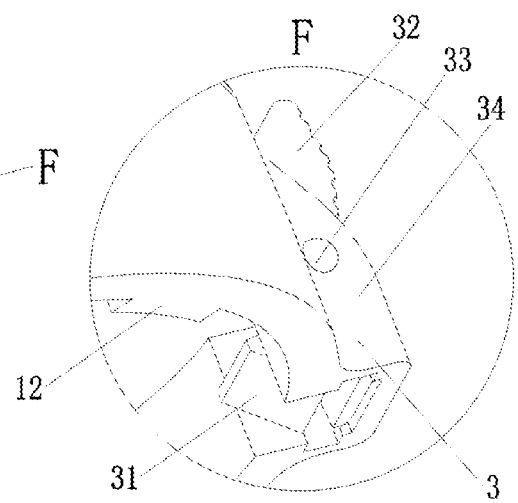
Figures 2, 3, 4:
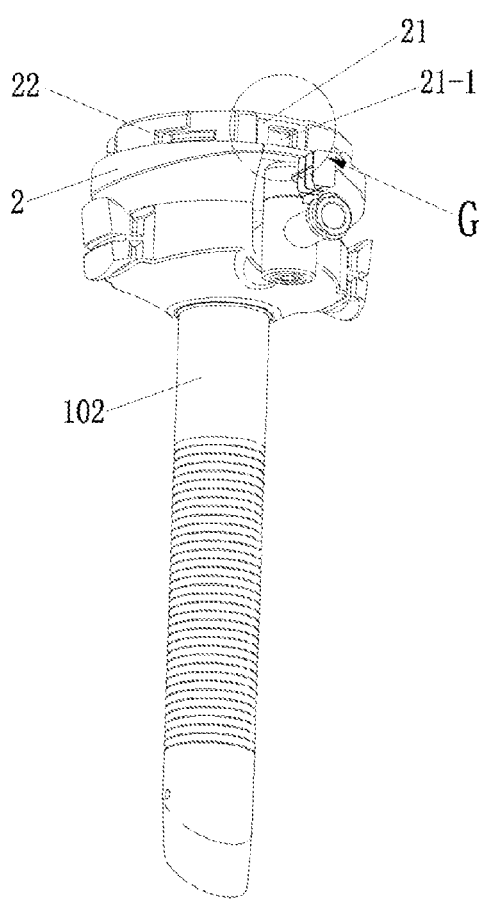
Figures 2, 3, 4, 5:
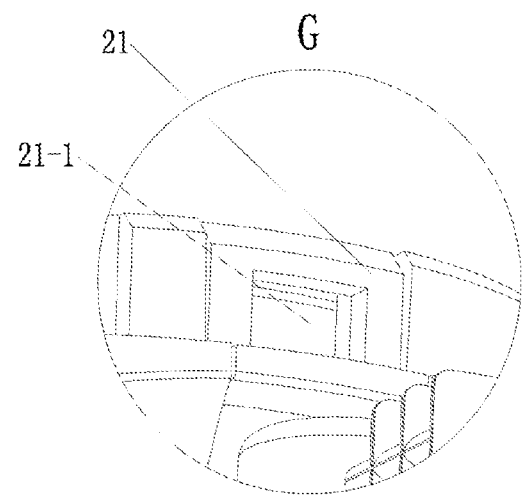
Figures 2, 3, 4, 5, 6:
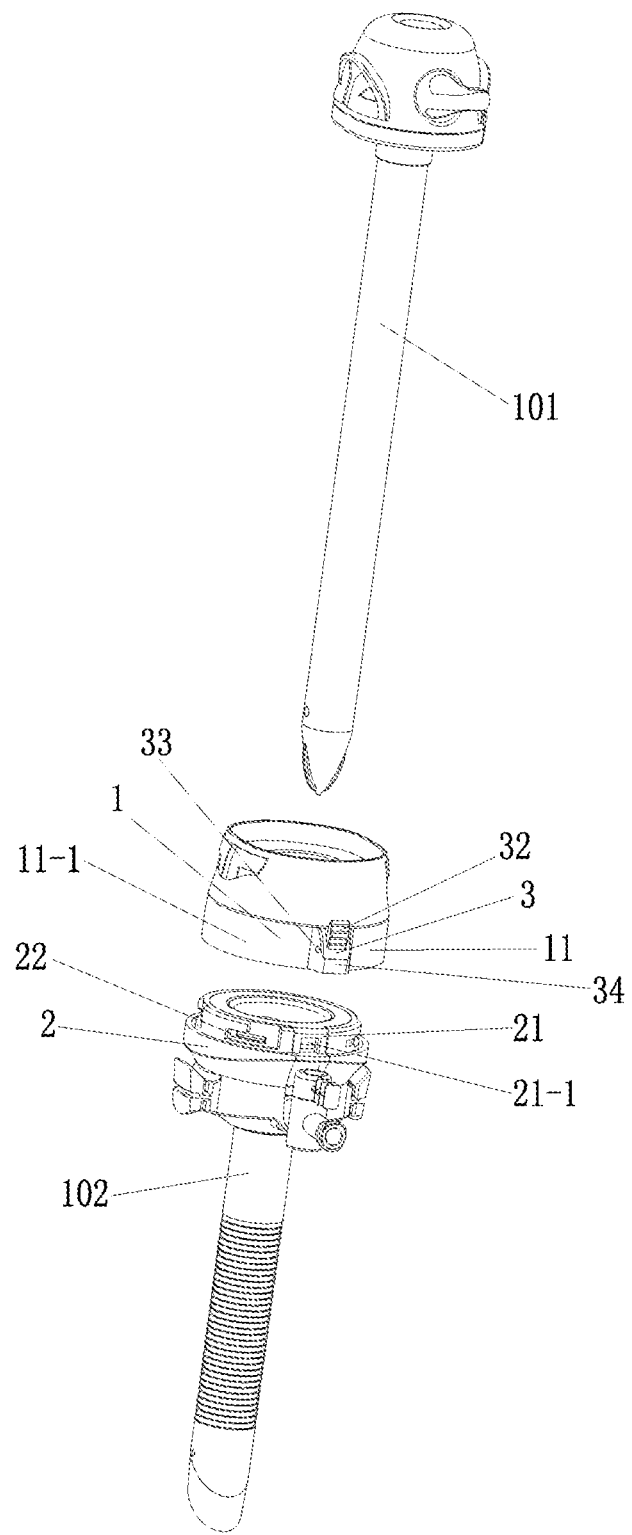

Embodiment 1: An Engagement Type Anti-Reverse Apparatus and a Trocar of the Present Application Referring to FIG. 1 to FIG. 1-7, an engagement type anti-reverse apparatus and a trocar are provided in the present application. The trocar 100 is composed of a trocar rod 101 and a sheath 102, the sheath 102 including an end sealing piece 1, a sleeve 2 and an anti-reverse apparatus 3. The end sealing piece 1 is detachably mounted on the sleeve 2. The anti-reverse apparatus 3 adopts an engagement type structure, and includes a latch 31 and a loose switch 32. The latch 31 is disposed on a side surface 21 of a near end of the sleeve, and engages with a positioning block 11-1 on a side surface 11 of a housing of the end sealing piece 1, such that the end sealing piece 1 may be only rotated clockwise and cannot be rotated anticlockwise. The loose switch 32 is disposed at a position, corresponding to the latch 31, on the side surface 11 of the housing of the end sealing piece 1. When the loose switch 32 is pressed down, the latch 31 is pressed down, the latch 31 no longer engages with the positioning block 11-1, and the end sealing piece 1 can be rotated clockwise and can be rotated anticlockwise as well.

The anti-reverse apparatus 3 of the present application includes a latch 31 capable of stopping an end sealing piece 1 from moving reversely, and a loose switch 32 capable of relieving a stopping action exerted by the latch 31 on the reverse movement of the end sealing piece 1. By pressing the loose switch 32 down, limitation of the latch 31 on the reverse movement of the end sealing piece 1 can be relieved. When the end sealing piece 1 is detachably mounted at the near end of the sleeve 2 in a rotating manner, the latch 31 of the anti-reverse apparatus 3 can stop reverse movement resulting in loosening of the end sealing piece 1 and prevent air leakage or prevent the end sealing piece 1 from loosening from the near end of the sleeve 2. When the loose switch 32 is pressed down, limitation of the latch 31 on the reverse movement of the end sealing piece 1 can be relieved, and the end sealing piece 1 is detached from the near end of the sleeve 2.

The end sealing piece 1 of the trocar 100 of the present application can be detachably mounted at the near end of the sleeve 2 in a rotating manner. For example, the end sealing piece is rotated clockwise, a connecting convex step 12 of the end sealing piece 1 slides into a connecting concave groove 22 at the near end of the sleeve 2, and the end sealing piece 1 and the sleeve 2 are connected together in a concave-convex engagement manner. The latch 31 of the anti-reverse apparatus 3 warps up, and engages with a positioning block 11-1 on the end sealing piece 1, such that the end sealing piece 1 cannot be rotated anticlockwise, thus stopping reverse movement capable of resulting in loosening of the end sealing piece 1, namely anticlockwise rotation of the end sealing piece 1.

When the end sealing piece 1 of the trocar 100 of the present application needs to be detached from the near end of the sleeve 2, the loose switch 32 is pressed down, the latch 31 of the anti-reverse apparatus 3 is pressed down, and cannot engage with the positioning block 11-1 on the end sealing piece 1, such that the end sealing piece 1 can be rotated anticlockwise, that is, the end sealing piece 1 is detached from the near end of the sleeve 2 by means of reverse movement.

The anti-reverse apparatus 3 can stop reverse movement resulting in loosening of the end sealing piece 1 and prevent air leakage or prevent the end sealing piece 1 from loosening from the near end of the sleeve 2. The defects of a conventional trocar are overcome, and the reliability of the trocar is improved.

Embodiment 2: An Inlaid Type Anti-Reverse Apparatus and a Trocar of the Present Application Referring to FIG. 2 to FIG. 2-6, an inlaid type anti-reverse apparatus and a trocar are provided in the present application. The trocar 100 is composed of a trocar rod 101 and a sheath 102, the sheath 102 including an end sealing piece 1, a sleeve 2 and an anti-reverse apparatus 3. The end sealing piece 1 is detachably mounted on the sleeve 2. The anti-reverse apparatus adopts an inlaid structure, includes a latch 31 and a loose switch 32, and further includes a rotary shaft 33 and a shell 34. The latch 31 and the loose switch 32 are disposed at two ends of the rotary shaft 33. The rotary shaft 33 is mounted on the shell 34. The latch 31, the loose switch 32 and the shell 34 are disposed on a side surface 11 of a housing of the end sealing piece 1 separately. The latch 31 is inlaid in a positioning concave groove 21-1 of a side surface 21 of a near end of the sleeve 2 to form inlaid concave-convex engagement positioning, and the end sealing piece 1 cannot be rotated clockwise and cannot be rotated anticlockwise as well. By pressing the loose switch 32 down, the latch 31 can be pulled out of the positioning concave groove 21-1, limitation on movement of the end sealing piece is relieved, and the end sealing piece 1 can be rotated clockwise and can be rotated anticlockwise as well.

The inlaid anti-reverse apparatus 3 of the present application includes a latch 31 capable of stopping an end sealing piece 1 from moving reversely, and a loose switch 32 capable of relieving a stopping action exerted by the latch 31 on the reverse movement of the end sealing piece 1. By pressing the loose switch 32 down, limitation of the latch 31 on the reverse movement of the end sealing piece 1 can be relieved. When the end sealing piece 1 is detachably mounted at the near end of the sleeve 2 in a rotating manner, the latch 31 of the anti-reverse apparatus 3 can stop reverse movement resulting in loosening of the end sealing piece 1 and prevent air leakage or prevent the end sealing piece 1 from loosening from the near end of the sleeve 2. When the loose switch 32 is pressed down, limitation of the latch 31 on the reverse movement of the end sealing piece 1 can be relieved, and the end sealing piece 1 is detached from the near end of the sleeve 2.

The end sealing piece 1 of the trocar 100 of the present application can be detachably mounted at the near end of the sleeve 2 in a rotating manner. After the loose switch 32 is pressed down, the end sealing piece is rotated clockwise, a connecting convex step 12 of the end sealing piece 1 slides into a connecting concave groove 22 at the near end of the sleeve 2, and the end sealing piece 1 and the sleeve 2 are connected together in a concave-convex engagement manner. After the loose switch 32 is loosened, the latch 31 of the anti-reverse apparatus 3 is inlaid in the positioning concave groove 21-1, such that the end sealing piece 1 cannot be rotated, thus stopping reverse movement capable of resulting in loosening of the end sealing piece 1, namely anti-clockwise rotation of the end sealing piece 1.

When the end sealing piece 1 of the trocar 100 of the present application needs to be detached from the near end of the sleeve 2, the loose switch 32 is pressed down, the latch 31 of the anti-reverse apparatus 3 is pulled out of the positioning concave groove 21-1, such that the end sealing piece 1 can be rotated anticlockwise, that is, the end sealing piece 1 is detached from the near end of the sleeve 2 by means of reverse movement.

The anti-reverse apparatus 3 can stop reverse movement resulting in loosening of the end sealing piece 1 and prevent air leakage or prevent the end sealing piece 1 from loosening from the near end of the sleeve 2. The defects of a conventional trocar are overcome, and the reliability of the trocar is improved.

Besides, the end sealing piece 1 is detachably mounted at the near end of the sleeve 2 by means of a rotary inlaid type concave-convex engagement structure, or the end sealing piece 1 is detachably mounted at the near end of the sleeve 2 by means of a threaded structure, and various specific anti-reverse apparatuses are designed. Those skilled in the art may also propose other specific designs according to the technical solution of the present application.

It should be noted that, the structures disclosed and illustrated in the description may be replaced by other structures with same effect, and meanwhile, the embodiments introduced in the present application are not the unique structure implementing the present application. Although preferable embodiments of the present application are already introduced and illustrated in the specification, but it is clearly known by those skilled in the art that the embodiments are merely examples, and those skilled in the art can make innumerable change, improvement and replacement without departing from the present application. Therefore, the protection scope of the present application shall be limited according to the spirit and scope of claims accompanied by the present application.

What is claimed is:

1. A trocar, comprising:
   a trocar rod; and
   a trocar sheath, including:
   a sleeve,
   an end sealing piece detachably mounted at a near end of the sleeve, and
   an anti-reverse apparatus that includes:
   a latch disposed on the sleeve, and
   a loose switch disposed on the end sealing piece
   wherein the latch is capable of stopping the end sealing piece from moving reversely by warping the loose switch radially-outward and engaging a positioning block of the end sealing piece, and
   wherein the loose switch is capable of relieving a stopping action exerted by the latch on the reverse movement of the end sealing piece in response to a radially-inward force applied to the loose switch.

2. The trocar according to claim 1, wherein the latch is disposed on a side surface of the near end of the sleeve, and the loose switch is disposed on a side surface of a housing of the end sealing piece, the loose switch corresponding to the latch in position.

3. The trocar according to claim 1, wherein the end sealing piece is detachably mounted at the near end of the sleeve by means of a rotary inlaid type concave-convex engagement structure.

4. The trocar according to claim 1, wherein the end sealing piece is detachably mounted at the near end of the sleeve by means of a threaded structure.

* * * * *